(12) United States Patent
Fischell et al.

(10) Patent No.: US 6,468,263 B1
(45) Date of Patent: *Oct. 22, 2002

(54) IMPLANTABLE RESPONSIVE SYSTEM FOR SENSING AND TREATING ACUTE MYOCARDIAL INFARCTION AND FOR TREATING STROKE

(75) Inventors: Robert E. Fischell, Dayton, MD (US); David R. Fischell, Fair Haven, NJ (US); Tim A. Fischell, Richland, MI (US)

(73) Assignee: Angel Medical Systems, Inc., Fair Haven, NJ (US)

(*) Notice: Subject to any disclaimer, the term of this patent is extended or adjusted under 35 U.S.C. 154(b) by 0 days.

This patent is subject to a terminal disclaimer.

(21) Appl. No.: 09/860,693

(22) Filed: May 21, 2001

(51) Int. Cl.⁷ .................................................. A61K 9/22
(52) U.S. Cl. .......................... 604/890.1; 600/517; 607/3
(58) Field of Search ............................... 604/890.1, 65, 604/66, 891.1; 607/30, 5, 9, 63, 2.4, 25, 32, 60, 62; 600/341, 517, 523

(56) References Cited

U.S. PATENT DOCUMENTS

| | | | |
|---|---|---|---|
| 3,888,260 A | 6/1975 | Fischell ................ 128/419 PG |
| 4,223,678 A | 9/1980 | Langer et al. .......... 128/419 D |
| 4,295,474 A | 10/1981 | Fischell ....................... 128/697 |
| 4,373,527 A | 2/1983 | Fischell ....................... 128/260 |
| 4,658,830 A | 4/1987 | Sarnoff ........................ 128/696 |
| 5,113,869 A | 5/1992 | Nappholz et al. ........... 128/696 |
| 5,135,004 A | 8/1992 | Adams et al. ............... 128/696 |
| 5,313,953 A | 5/1994 | Yomtov et al. .............. 128/696 |
| 5,531,768 A | 7/1996 | Alferness ........................ 607/6 |
| 5,634,899 A | * 6/1997 | Shapland et al. .............. 604/51 |
| 5,800,498 A | 9/1998 | Obino et al. ................. 607/123 |
| 5,925,066 A | * 7/1999 | Kroll et al. |
| 6,049,736 A | * 4/2000 | Stewart et al. ............... 604/116 |
| 6,112,116 A | * 8/2000 | Fischell et al. .............. 600/517 |
| 6,122,536 A | * 9/2000 | Sin et al. ...................... 600/341 |
| 6,126,038 A1 | * 4/2001 | Hartlaub et al. ............... 607/31 |
| 6,272,379 B1 | * 8/2001 | Fischell |

* cited by examiner

Primary Examiner—Brian L. Casler
Assistant Examiner—Kevin C. Sirmons

(57) ABSTRACT

Disclosed is a completely implantable system that can detect the occurrence of a myocardial infarction, i.e., a heart attack, and automatically inject a thrombolytic and/or anti-thrombogenic agent into the bloodstream to promptly dissolve the thrombus that caused the myocardial infarction and prevent the formation of additional thrombi. It is well known that a myocardial infarction can be detected from a patient's electrocardiogram by noting an ST segment voltage deviation. Upon detection of a myocardial infarction, an ST segment deviation electronic detection circuit within the implanted device can produce an output signal that can cause a thrombolytic and/or anti-thrombogenic agent contained within an implanted, pressurized reservoir to immediately and automatically release medications into the patient's bloodstream. A patient warning system is also provided by an audio alarm or an electrical tickle within the human body indicating that a myocardial infarction has been detected. An externally located part of the system, in the form of a patient operated initiator, can be used to trigger the release of medication as soon as a first sign of a stroke has been detected in order to prevent damage to brain tissue that would be caused by that stroke. Thus the system can be used to prevent trissue damage from either a myocardial infarction or a stroke. The implanted system can also send a radio message to an externally located receiver that automatically dials an emergency rescue team to take the patient to a hospital for continuing treatment of a myocardial infarction or a stroke.

39 Claims, 6 Drawing Sheets

IMPLANTABLE RESPONSIVE SYSTEM FOR SENSING AND TREATING ACUTE MYOCARDIAL INFARCTION AND FOR TREATING STROKE

FIELD OF USE

This invention is in the field of devices implanted within a human body for the purpose of automatically detecting the onset of myocardial infarction, warning the patient that a myocardial infarction is occurring and promptly releasing medication into the bloodstream for the purpose of dissolving obstructive thrombus in a coronary artery thus ameliorating damage to the myocardial tissue which would otherwise occur. The invention also includes the capability for treating ischemic stroke.

BACKGROUND OF THE INVENTION

Heart disease is the leading cause of death in the United States. The most prevalent fatal manifestation of coronary heart disease is myocardial infarction which is caused primarily by a thrombus that obstructs blood flow in one or more coronary arteries. The medical treatment of myocardial infarction involves intravenous delivery of a thrombolytic medication such as tissue plasminogen activator (tPA) to help dissolve the thrombus in a coronary artery. The sooner thrombolytic medication is placed into the patient's bloodstream after the occurrence of a myocardial infarction, the sooner an obstructive thrombus will be dissolved and some perfusion of the myocardium can occur. The extent of permanent damage to the myocardium is highly dependent upon the length of time that occurs prior to restoration of blood flow to the heart muscle. However, at this time no implantable system exists that provides for early and automatic detection of myocardial infarction. Furthermore, no system exists that would provide automatic and immediate release of an anti-thrombogenic or thombolytic agent into the bloodstream to dissolve an obstructive blood clot at the earliest possible time and prevent the recurrence of a blood clot.

One of the most debilitating diseases to which human beings are subjected is thrombotic stroke that is caused by a blood clot blocking a cerebral artery. There are approximately 500,000 such strokes in the USA each year with a 30 day survival rate of less than 80%. The lifetime cost for treatment of each of these patients exceeds $90,000. Therefore, any treatment modality that could decrease brain damage from thrombotic stroke would be highly advantageous to the population of the USA and the rest of the world both from a health point of view and from a cost saving prospective.

Approximately 40% of stroke survivors will suffer a cardiovascular death. Furthermore, in the first few months after a myocardial infarction there is a 5% probability of stroke. However, there is no extant system that includes an implanted medication release device that can treat either or both a stroke or a myocardial infarction.

SUMMARY OF THE INVENTION

One embodiment of the present invention is a completely implantable system that can detect the occurrence of a myocardial infarction, i.e., a heart attack, within less than a minute after it begins and then automatically inject a thrombolytic and/or anti-thrombogenic agent into the bloodstream to promptly dissolve the thrombus that caused the myocardial infarction and to prevent the formation of additional thrombi.

It is well known that a myocardial infarction can be detected from a patient's electrocardiogram by noting an ST segment deviation (e.g., voltage increase) as compared to the voltage of the patient's TP or PQ segments. Such an ST segment deviation can be even more clearly discerned with electrodes implanted within the body (especially within or in close proximity to the heart) as compared with detecting the deviated ST segment from chest or limb mounted electrodes. The signal from the heart using implanted electrodes is called an "electrogram". By means of an electrogram, early detection of a thrombus causing myocardial ischemia is clearly feasible. Furthermore, the patient's level of $pO_2$ and/or his heart rate (each of which can be determined from an implanted part of the system) can also used either by itself for $pO_2$ or in conjunction with ST segment deviation (for $pO_2$ and heart rate) to verify the presence of a myocardial infarction as opposed to some other cause of coronary ischemia.

Upon detection of a myocardial infarction, an ST segment deviation electronic detection circuit within the implanted device can produce an output signal that can cause a thrombolytic and/or anti-thrombogenic agent contained within an implanted reservoir to immediately and automatically release medication into the patient's bloodstream. Thus, the thrombolytic agent is placed into the bloodstream for dissolving an obstructive thrombus at the earliest possible time. Therefore, both mortality and morbidity can be dramatically reduced. In fact, it is possible that such a system could significantly decrease the initial risk of a fatal ventricular arrhythmia as well as myocardial tissue necrosis that often progresses to congestive heart failure.

It is envisioned that additional embodiments of the present invention can include a patient warning system that informs the patient by either an audio alarm or by an electrical tickle within his body that a myocardial infarction has been detected and that a thrombolytic agent has been released. At the occurrence of such an alarm, the patient can be instructed to seek immediate medical care.

An additional embodiment of the present invention is for the implanted system to send a radio message to a receiver within the patient's home that automatically dials an emergency rescue team to take the patient to a hospital for continuing treatment of his myocardial infarction.

Still another embodiment of the invention includes either an implanted defibrillator or heart pacemaker that would be used in conjunction with the system for automatic release of a thrombolytic agent.

Although the previous discussion addresses only the situation involving a myocardial infarction, it would be highly advantageous to have an implanted system that can treat either or both a myocardial infarction or a thrombotic stroke. The implanted portion of such a system is defined herein as a cardiosaver-strokesaver device. The entire system including portions that are not implanted within the patient is defined herein as a cardiosaver-strokesaver system. It is also envisioned that a cardiosaver-strokesaver device could be combined with a conventional implantable defibrillator and/or pacemaker. The combined capability of the cardiosaver-strokesaver system would be capable of automatically introducing an anti-thrombogenic or thrombolytic drug into the patient's vascular system if a myocardial infarction is detected or the drug could be administered by the patient or by someone close to the patient if an early symptom of a stroke is detected. These early symptoms of a stroke that could be used to trigger the release of medication are: (1) sudden weakness or numbness of the face, arm or leg on one side of the body: (2) sudden dimness or loss of vision, especially in one eye; (3) loss of speech or trouble talking or understanding speech; (4) sudden and severe headache with no apparent cause; and (5) an unexplained dizziness, unsteadiness or sudden falls. The patient and/or a person living with or taking care of the patient (collectively the patient caregiver) would be taught all of these early signs of a stroke. At the onset of any such early sign, the patient or the patient caregiver would use a patient operated initiator to trigger the release of a medication from the implanted cardiosaver-strokesaver device to restore patentcy to the cerebral artery that has a thrombotic blockage. Thus, the cardiosaver-strokesaver device would have the capability to automatically release medication to treat a myocardial infarction and would also have the capability to release medication by action of the patient operated initiator to prevent brain damage in the event of a stroke.

Patient selection for such a cardiosaver-strokesaver system is of great importance. It is anticipated the cardiosaver-strokesaver system could be part of any pacemaker and/or automatic defibrillator that is implanted into any human subject that requires such a device. Furthermore, the cardiosaver-strokesaver system would be advantageously placed in any human subject who has one or more of the following conditions: (1) atherosclerosis; (2) hypercholesterolemia; (3) high blood pressure: (4) a family history of myocardial infarction; (5) a family history of stroke; (6) transient ischemic attacks (TIA's); (7) a prior myocardial infarction; (8) a prior stroke; (9) diabetes; or (10) untreatable atrial defibrillation.

Thus it is an object of this invention to have an implanted system that releases a thrombolytic and/or anti-thrombogenic agent into the bloodstream of a human body upon detection of either a myocardial infarction or a stroke.

Another object of this invention is to automatically inform the patient that a myocardial infarction has occurred by means of an alarm such as a subcutaneous electrical tickle or audio signal.

Still another object of this invention is to utilize the automatic myocardial infarction detection and medication release system (the cardiosaver portion) and the manually activated system to release medication to treat the early symptoms of a stroke (the strokesaver portion) in conjunction with an implantable defibrillator and/or pacemaker.

Still another object of this invention is to have an implanted defibrillator or pacemaker that includes sensors (such as electrodes) to sense a myocardial infarction and to trigger an internal alarm and an externally located alarm to inform the patient that he has the indication of a myocardial infarction. This system could provide specific instructions for self-administration of additional medications.

Still another object of this invention is to have a combined cardiosaver-strokesaver system that sends a radio signal to a receiving system located in close proximity to the patient which then makes a telephone call to a rescue service that sends an ambulance to bring the patient to a hospital.

Still another object of this invention is to have an implantable myocardial infarction detection system that sends a radio signal to a receiving system in the patient's home that informs the patient that he may be undergoing a myocardial infarction and that an ambulance has been called to bring him to a hospital and that he should take certain actions such as taking an aspirin tablet.

Still another object of the invention is to use more than one physiological parameter (such as any combination of ST segment deviation, $pO_2$, heart rate, etc.) to verify the occurrence of a myocardial infarction.

Still another object of this invention is to provide a patient with a patient operated initiator which he could use to initiate the release of one or more medications that have been placed into the implanted portion of the cardiosaver-strokesaver system.

Still another object of this invention is to provide a means for informing the patient that he is having a myocardial infarction when he might otherwise ignore some particular symptom or he may not have perceived any symptom.

Still another object of this invention is to have an implantable system for the detection of a myocardial infarction that also has the capability for storing electrograms.

These and other objects and advantages of this invention will become obvious to a person of ordinary skill in this art upon reading of the detailed description of this invention including the associated drawings as presented herein.

DETAILED DESCRIPTION OF THE DRAWINGS

Figure 1:
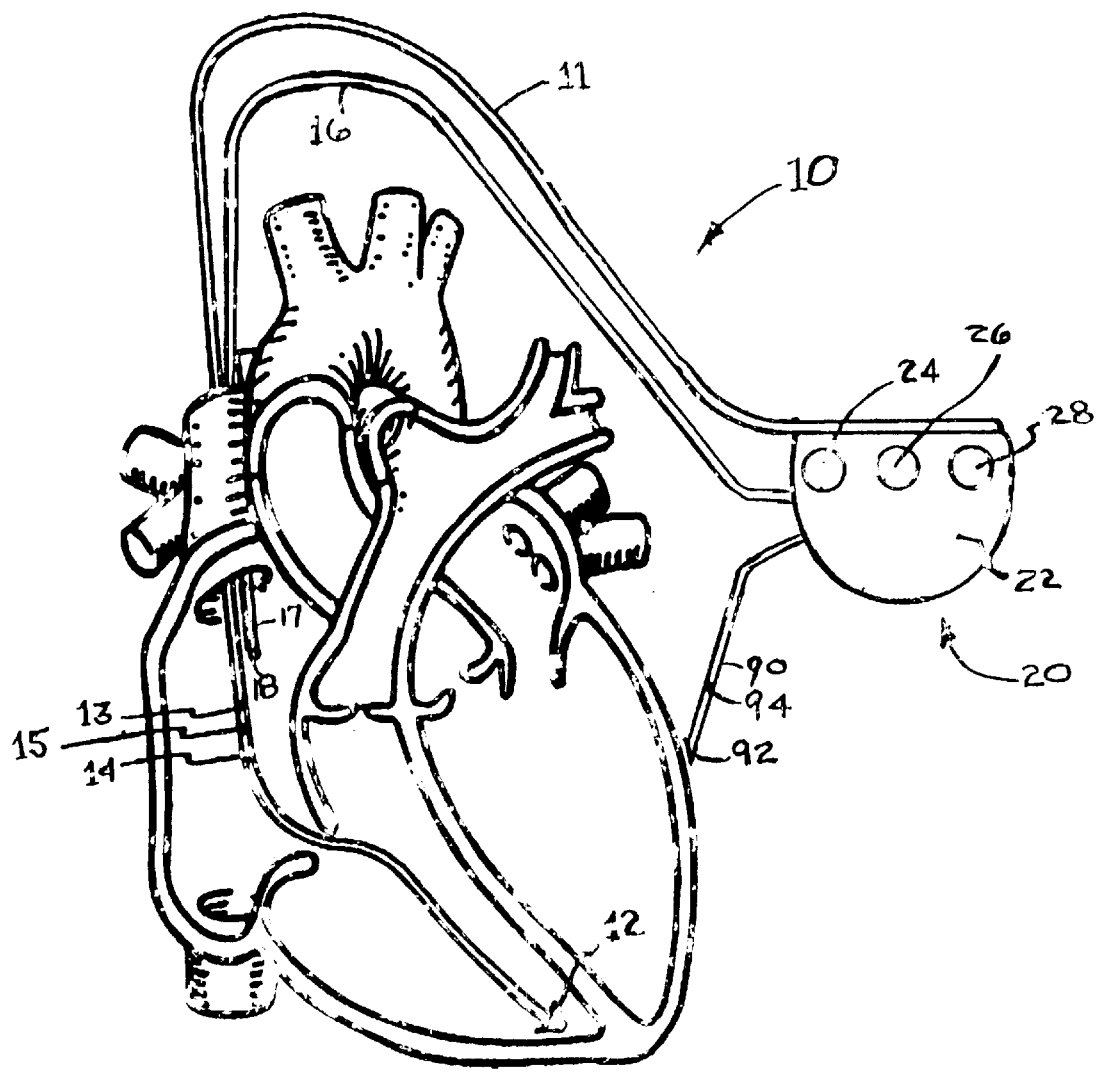
FIG. 1 illustrates an implantable system for the automatic detection of a myocardial infarction and for the injection into the bloodstream of one or more thrombolytic and/or anti-thrombogenic medications for the automatic treatment of myocardial infarction or the manual (i.e., patient initiated) treatment of stroke.

FIG. 1 illustrates an arrangement of the present invention which is an automatic responsive myocardial infarction treatment system and/or the implanted portion of a system for manually treating any early symptom of a stroke; this system being a medication release system 10. The system 10 includes a medication release device 20 having a case 22 and as many as three medication reservoir entry ports 24, 26 and 28 and three catheters 11, 16 and 90. Each of the three catheters 11, 16 and 90 can be either an electrical lead or a medication delivery catheter or both. For example, the catheter 11 has a distal electrode 12, proximal bipolar electrodes 13 and 14, and a medication exit port 15. The catheter 16 has a single electrode 17 located near the catheter's distal end and a medication exit port 18 at the catheter's distal end. The catheter 90 has electrodes 92 and 94. The catheter 11 and/or the catheter 16 would be placed through the patient's venous system with each catheter's distal end being placed at or near the apex of the right ventricle, or in the right atrium, or in the superior vena cava as would be typical for a pacemaker or defibrillator lead. The catheter 90 would be placed under the skin with the electrodes 92 and 94 being situated in reasonably close proximity to the heart.

It should be understood that the system 10 could use only one catheter, e.g., the catheter 11 for all functions. All functions would include electrogram detection, application of a pacing pulse or defibrillation shock and injection of a medication such as a thrombolytic agent. The system 10 might also use two catheters such as the catheters 11 and 16. One catheter could be used for medication delivery and the other could be used for electrical functions. The system 10 could also use one electrode such as either electrode 12 or 92 as an active electrode and use the case 22 of the medication release device 20 as an indifferent or ground electrode. One important aspect of the system 10 is that the medication can be delivered into the patient's arterial circulation. It is believed that intra-arterial administration of a thrombolytic agent or anti-thrombogenic medication can be advantageous for the treatment of either a myocardial infarction or a stroke as compared to intravenous administration of the medication.

Figure 2:
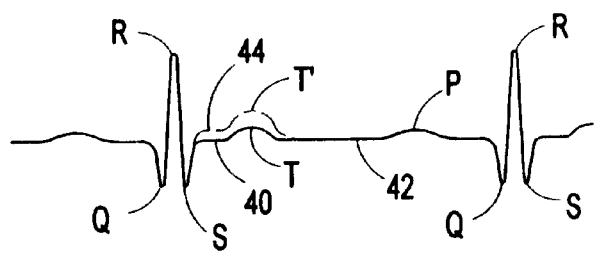
FIG. 2 illustrates a normal electrogram pattern and also shows an elevated ST segment deviation which would be indicative of a myocardial infarction.

FIG. 2 illustrates a typical electrogram signal from some pair of implanted electrodes such as the electrode 12 and the case 22 of FIG. 1. The various portions of the electrogram are shown as the Q,R,S, T and P waves. These are all shown as portions of a solid line in FIG. 2. The normal ST segment 40 is also shown in FIG. 2. When a myocardial infarction occurs, there is a deviation of the ST segment 44 as shown by the dotted lines in FIG. 2. It is this deviation of the ST segment 44 as compared to the not deviated segment 42 that is a clear indicator of a myocardial infarction. Furthermore, it should be understood that the ST segment deviation could be either positive or negative depending upon where the electrogram electrodes are located and where in the myocardium the infarction has occurred. Although a deviated ST segment 44 can be a good indicator of a myocardial infarction, other indicators such as heart rate, heart wall motion or blood pO$_2$ could also be used as independent sensing means. These means could be used in addition to a deviated ST segment 44 to improve the reliability for detection of a myocardial infarction.

Figure 3:
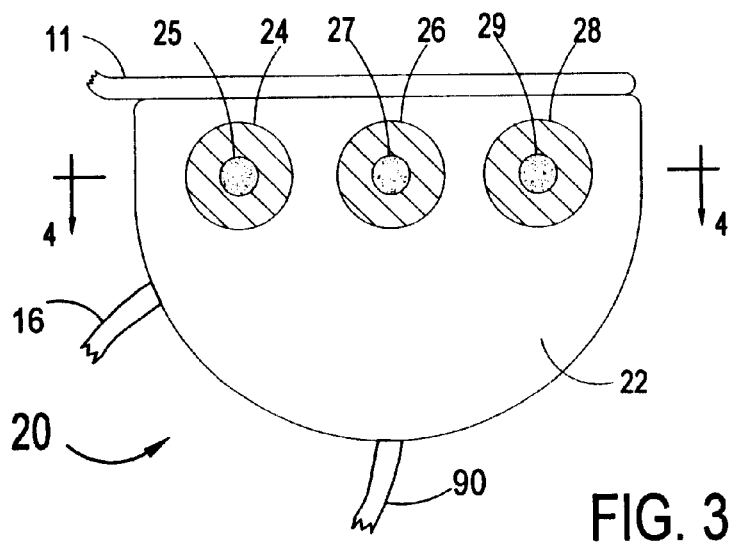
FIG. 3 is a plan view of the medication release device which is part of the system for early detection of a myocardial infarction and for the release of one or more medications.

FIG. 3 is a plan view of the medication release device 20 having a metal conducting case 22 and three medication entry ports 24, 26 and 28 each of which has respectively self-sealing septums 25, 27 and 29. The medication release device 20 also has catheters 11, 16 and 90 which can serve as electrical leads and/or medication release catheters.

Figure 4:
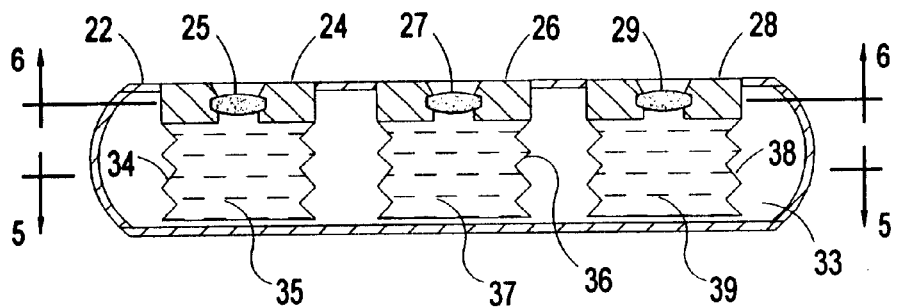
FIG. 4 is a cross section of the medication release device at section 4—4 of FIG. 3 showing three separate medication reservoirs.

FIG. 4 is a cross section of the medication release device 20 at section 4—4 of FIG. 3. FIG. 4 shows three medication reservoirs 35, 37 and 39 which have respectively medication entry ports 24, 26 and 28, self-sealing septums 25, 27 and 29 and thin-walled metal bellows 34, 36 and 38 that form medication enclosures. It should be understood that the medication release device 20 could have as few as one or as many as three separate medication reservoirs for thrombolytic agents, or agents that prevent platelet aggregation, or agents (such as nitroglycerin) that produce vascular dilation. The thrombolytic agents could be tissue plasminogen activator (tPA), urokinase or streptokinase. Agents that are anti-thrombogenic could be the drug ReoPro, heparin, Integrillin, Plavix or others. It is also conceived that an anti-arrhythmic medication could also be placed in one of the reservoirs 35, 37 or 39.

FIG. 4 also shows the metal case 22 having an interior chamber 33. All the metal parts shown in FIG. 4 would preferably be formed from titanium. The septums 25, 27 and 29 would preferably be formed from a low durometer elastomer such as neoprene rubber that is placed in compression by the entry ports 24, 26 and 28. The chamber 33 should contain a pressurized inert gas such as helium. Thus, even though the metal bellows can exert a pressure of several psi within the reservoirs 35, 37 and 39, by pressurizing the chamber 33 with between 5 and 50 psi, there is an enhanced pressure that can cause the medications to be quickly released when an outlet valve is opened. It may also be desirable to place a few drops of a liquid such as Freon 21 into the chamber 33 instead of an inert gas. This would have the effect of maintaining a constant pressure of approximately 39 psi in the chamber 33 irrespective of whether the bellows 34, 36 and 38 were fully extended or fully contracted.

Figure 5:
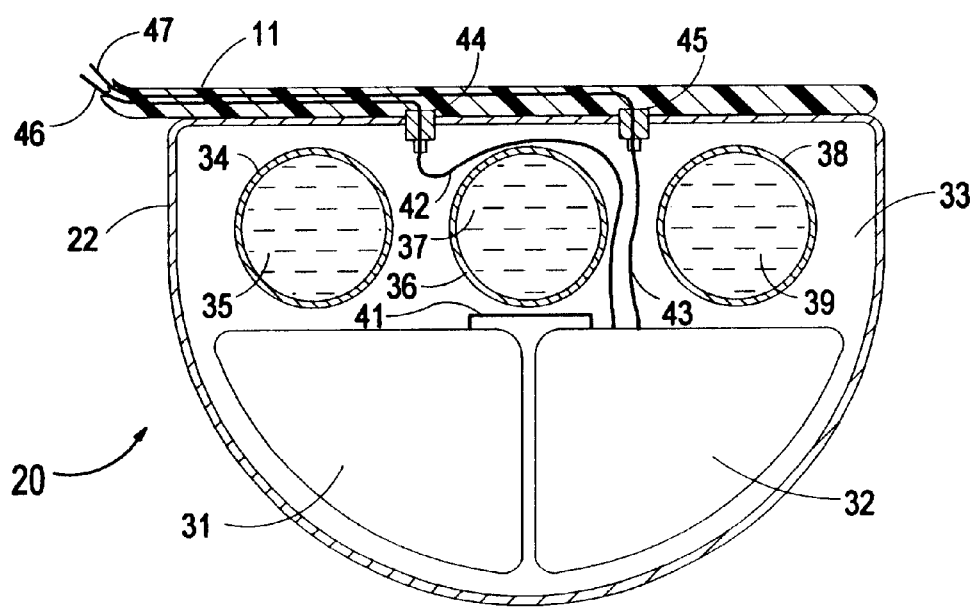
FIG. 5 is a cross section of the medication release device at section 5—5 of FIG. 4.

FIG. 5 is a cross section of the medication release device 20 at section 5—5 of FIG. 4. FIG. 5 shows the bellows 34, 36 and 38 that enclose respectively the medication reservoirs 35, 37 and 39 all within the case 22. Although three reservoirs are shown in FIG. 5, it is certainly possible to have more than three reservoirs. Also shown in FIG. 5 is a battery 31 that is connected to an electronics module 32 by the wire 41. The wires 42 and 43 connect the electronics module 32 to the wires 46 and 47 through the electrical feed-thrus 44 and 45 in the case 22. The wires 46 and 47 within the catheter 11 can be connected to the electrodes 12 and 14 as shown in FIG. 1.

Figure 6:
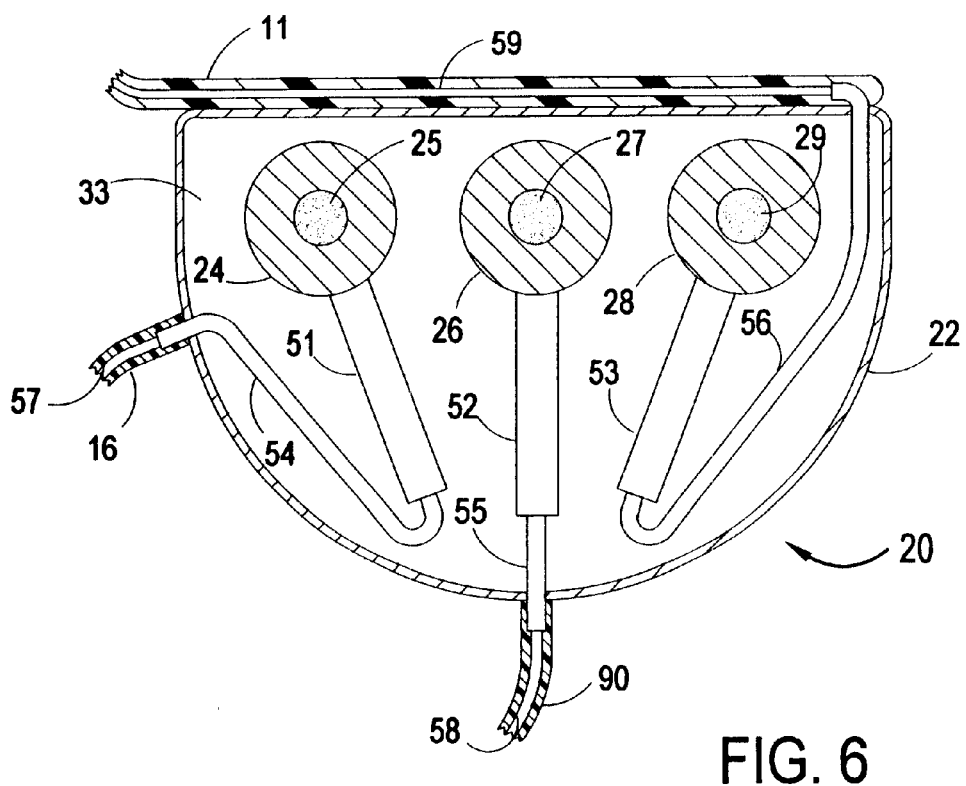
FIG. 6 is a cross section of the medication release device at section 6—6 of FIG. 4.

FIG. 6 is cross section at section 6—6 of FIG. 4. FIG. 6 shows the entry ports 24, 26 and 28 having respectively septums 25, 27 and 29 and release valve assemblies 51, 52 and 53 each connected respectively to output tubes 54, 55 and 56. The medications from the release valve assemblies 51, 52 and 53 pass out into the patient's bloodstream via the lumen 57 in the catheter 16, or through a lumen 59 in the catheter 11 or through the lumen 58 in the catheter 90. The pressurized chamber 33 is also shown in FIG. 6. It is also envisioned that the outlet tubes 51, 52 and 53 could be connected into a single catheter.

Figure 7:
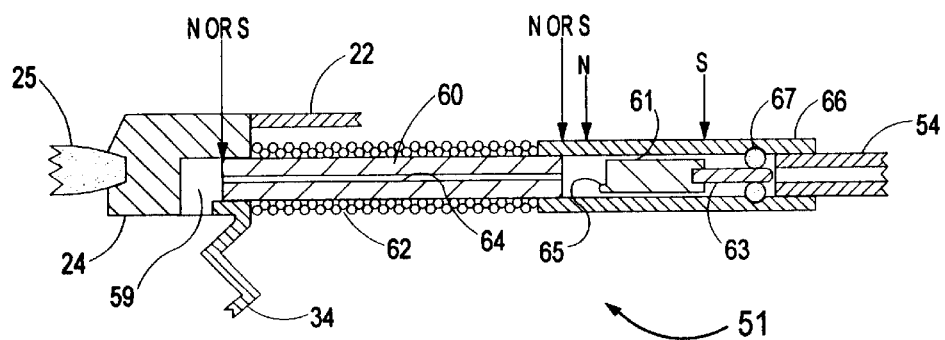
FIG. 7 is a longitudinal cross section of a magnetic system to release medication into the bloodstream from an implantable reservoir of the medication release device.
Figure 8:
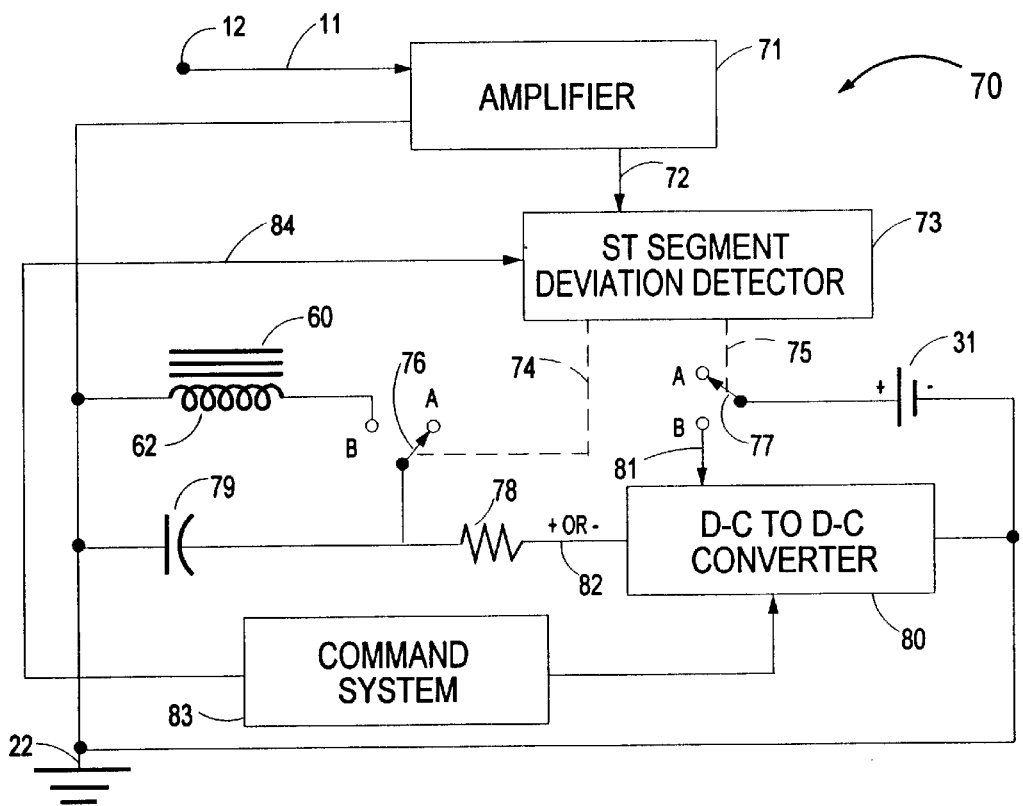
FIG. 8 is a block diagram of that part of the electrical system of the medication release device whose function is to detect a myocardial infarction and release appropriate medication(s).

FIG. 7 is a longitudinal cross section of the medication release assembly 51 that is fixedly attached to the entry port 24 into which the septum 25 has been placed. The medication release assembly 51 consists of a chargeable magnet 60 having an electrical charging coil 62 and a small diameter central lumen 64. By appropriately discharging a capacitor through the coil 62, the chargeable magnet 60 can have its polarity reversed at each end from north to south or from south to north. This operation is best explained with reference to FIG. 8. In FIG. 8 we see that when the switch 77 is placed at its terminal B, the battery 31 is electrically connected to the d-c to d-c converter 80. This causes the capacitor 79 to become fully charged over a certain period of time depending on the value of the resistor 78. Then, when the switch 76 is moved from its terminal A to terminal B, the capacitor 79 discharges through the charging coil 62 that is placed around the chargeable magnet 60 which causes the chargeable magnet 60 to become permanently magnetized with a specific polarity. If, let us say, this was accomplished with a positive voltage out of the d-c to d-c converter 80, then the direction of the winding of the coil 62 could be adjusted to make the right end of the chargeable magnet 60 (as seen in FIGS. 7 and 8) a north pole. If the command system 83 causes the output voltage of the d-c to d-c converter to be negative, then when the capacitor 79 is charged and then discharged through the charging coil 62, the chargeable magnet 60 will have the a south pole at its right end. Thus, the command system 83 from an external signal (as will be explained with the help of FIG. 9) can cause the chargeable magnet 60 to have either a north or south polarity at its right end. A permanent magnetic material having a comparatively low coercive force, such as Vicalloy, would be ideal for the chargeable magnet 60. A permanent magnet material having a high coercive force and a high energy product, such as Alnico V, would be ideal for the permanent magnet 61.

Returning now to a discussion of FIG. 7, when the chargeable magnet 60 has a north pole at its right end, it will repel the adjacent north pole of a permanent magnet 61 that is placed within the tube 66. Thus, a highly polished cylinder 63 will be pushed through the O-ring 67 which forms a pressure tight seal to prevent any medication that is within the bellows 34 from going into the exit tube 54. When the polarity of the chargeable magnet 60 is reversed (as has been explained with the assistance of FIG. 8), then the right end of the chargeable magnet 60 will be a south pole and it will attract the north pole at the left end of the permanent magnet 61. This will cause the cylinder 63 to be pulled out of the O-ring 67 which will cause the pressurized fluid from within the bellows 34 to be passed through the port 59, through the lumen 64 of the chargeable magnet 60 and then through the annular passageway that exists between the exterior surface of the permanent magnet 61 and the interior surface of the tube 66. The medication then will pass through the O-ring 67 and into the exit tube 54. It should be noted that a small protrusion 65 at the left end of the permanent magnet 61 allows a fluid passageway to be maintained between the right end of the chargeable magnet 60 and the left end of the permanent magnet 61.

Although FIG. 7 shows a means for promptly releasing medication into the bloodstream using a chargeable magnet system, it should be understood that other means such as the use of a solenoid valve operated either from a battery or a capacitor could also be used. Furthermore, the use of a conventional implantable drug pump such as taught in the U.S. Pat. No. 4,373,527 by R. E. Fischell, or any similar implantable drug pump could be used instead of the medication delivery system that is described herein.

After the medication (such as a thrombolytic agent) is sent out through the exit tube 54, the polarity of the chargeable magnet 60 can be reversed which would push the cylinder 63 back through the O-ring 67 thus resealing the medication release device. The bellows 34 could then be refilled with a medication by use of a syringe with a non-coring needle that would be placed through the septum 25. Therefore, after a patient has experienced a myocardial infarction that results in the discharge into his bloodstream of some medication, one or more of the medication reservoirs 35, 37 or 39 could be refilled for use during a subsequent myocardial infarction.

FIG. 8 is a block diagram of the medication delivery electronic circuitry 70 that would (for the most part) be contained within the electronics module 32 shown in FIG. 5. The circuitry 70 has the explicit function of detecting a myocardial infarction and responding with the delivery of one or more medications into the patient's bloodstream to dissolve the thrombus that caused the myocardial infarction. Specifically, the medication delivery electronic circuitry 70 uses an electrode 12 that is electrically connected to an amplifier 71 by means of a wire in the catheter 11. The amplified electrogram signal is sent over the line 72 to an ST segment deviation detector 73. When an elevated or depressed ST segment is detected (as shown in FIG. 2), the detector 73 has an output 75 that causes the switch 77 to move from terminal A to terminal B. As previously described, this causes the d-c to d-c converter 80 to turn on and charge the capacitor 79. When the capacitor 79 is charged, the ST deviation detector 73 then uses the output line 74 to move the switch 76 from terminal A to terminal B. This, as previously described, causes a pulse of electric current to flow through the coil 62 to magnetize the chargeable magnet 60 in a polarity to cause discharge of (typically) some thrombolytic agent into the patient's bloodstream. After this is accomplished, the command system 83 can receive a command from a physician's programmer (element 108 of FIG. 9) that results in a signal on line 84 to reset the switches 76 and 77 and to reset the d-c to d-c converter to have an opposite output polarity. As seen in FIG. 8, the electrode 12 would act as an active electrode and the case 22 would act as a ground or indifferent electrode. Of course it should be understood that the switches 76 and 77 would be in the form of transistor switches that are well known in the field of electrical circuit design.

Figure 9:
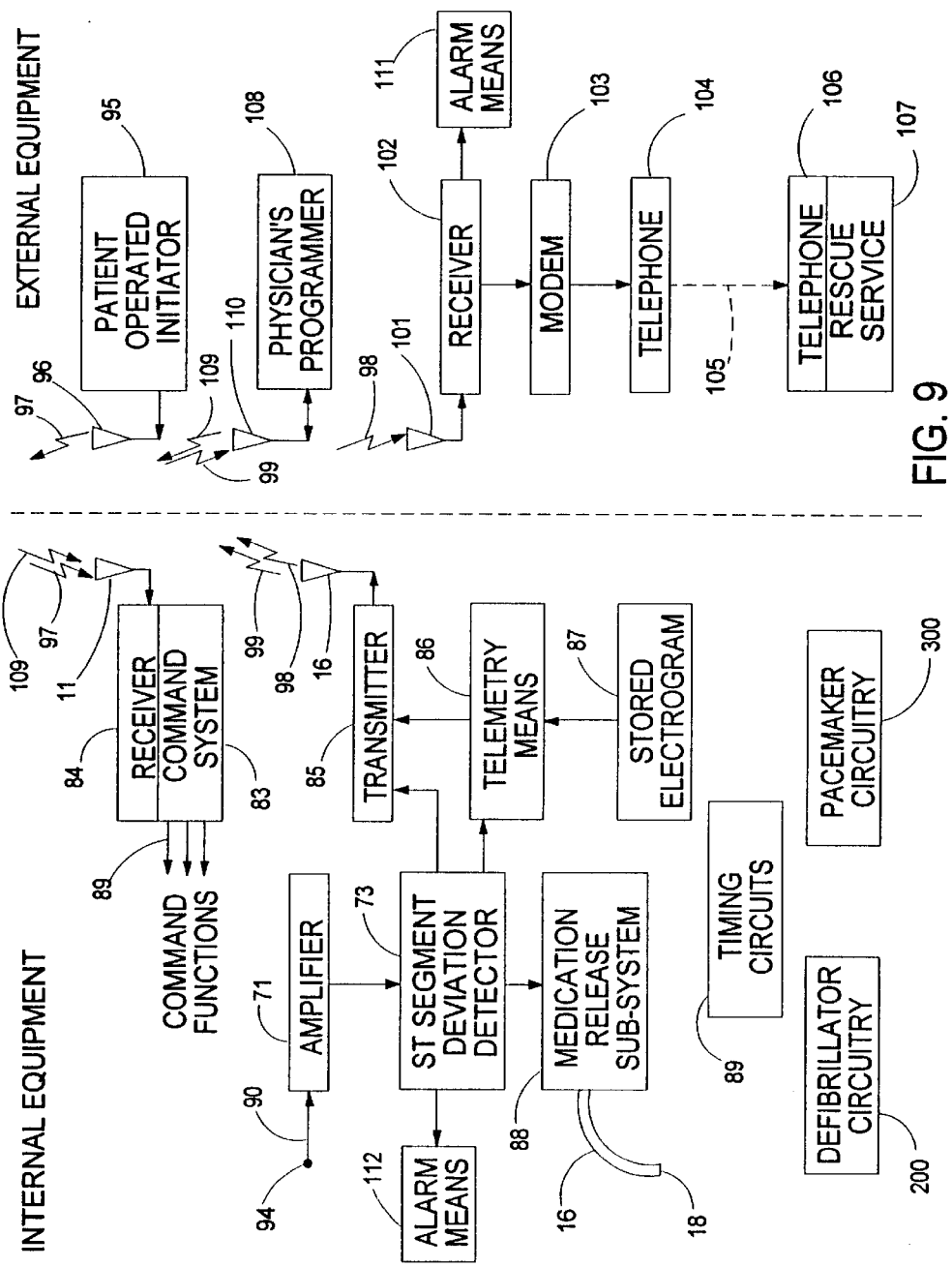
FIG. 9 is a system block diagram that illustrates the arrangement of equipment that can be implanted in the patient and other equipment that can be placed external to the patient for the treatment of myocardial infarction and/or stoke.

FIG. 9 is a block diagram of a more elaborate embodiment of a system for the prompt and automatic treatment of myocardial infarction or the manually actuated treatment of stroke; i.e., the cardiosaver-strokesaver system. The left side of FIG. 9 shows the cardiosaver-strokesaver portion of the system that would be implanted in a patient who has a comparatively high probability for having either a myocardial infarction or a stroke. These would be patients who have already survived a first heart attack or stroke, or who have an implanted pacemaker or defibrillator, or who have undergone angioplasty or bypass surgery. Patients with advanced forms of insulin dependent diabetes, or who have athersclerosis, hypercholesterolemia or high blood pressure would also be good candidates for such a system.

The right side of FIG. 9 illustrates equipment that would be situated externally to the patient. This equipment would be used to manually actuate the implanted cardiosaver-strokesaver when at least one early sign of a stroke is detected. This manual actuation would be accomplished by the patient or by a patient caregiver, e.g., the patient's spouse or a nurse or attendant at a nursing home where the patient might reside. The catheter 11 in FIG. 9 can act by means of an electrical conductor within the catheter 11 as an antenna 11. This antenna 11 can have input radio signals 97 or 109 which are then fed into the command receiver 84 which is part of the command system 83. The radio signal 97 would emanate from the patient operated initiator 95 through its antenna 96. The patient operated initiator 95 can be used by the patient to trigger some event such as the release of medication or holding in memory a particular portion of a recorded electrogram signal that the patient believes might be relevant to his medical condition. The patient operated initiator 95 would be specifically used to manually trigger the release of a medication to treat any early symptom of a stroke. It is also envisioned that an implanted patient operated initiator (not shown) could be manually actuated by a human subject if an early symptom of a stroke is detected.

In FIG. 9, the radio signal 109 would emanate from the physician's programmer 108 through its antenna 110. The radio signal 109 as received by the antenna 11 of the implanted portion of the equipment would be an input to the command receiver 84 which, by means of the command system 83, can produce a multiplicity of command functions 89. Examples of these command functions 89 are as follows: move the switch 76 between terminals A and B, (see FIG. 8), move the switch 77 between terminals A and B, change the output voltage polarity of the d-c to d-c converter 80 from plus to minus or from minus to plus, adjust the threshold voltage at which a deviated ST segment is deemed to indicate a myocardial infarction, select one or more medication reservoirs to inject a thrombolytic agent into the bloodstream when a myocardial infarction is detected, enable defibrillator circuitry 200, enable pacemaker circuitry 300, check operating features of the implanted system such as battery voltage, etc.

FIG. 9 also shows a terminal 94 which feeds an electrogram signal through a conducting wire in the catheter 90 into an amplifier 71 whose output is fed into the ST segment deviation detector 73. When the ST segment deviation qualifies as an indication of a myocardial infarction, the ST segment deviation detector 73 provides an output triggering signal into the medication release sub-system 88 that releases medication through the catheter 16 (see FIG. 1) and out of the opening 18 into the patient's bloodstream. When the start of a myocardial infarction is detected by the implantable equipment, or when the patient operated initiator 95 is used to signal that a stoke is occurring, a radio signal 98 is sent out of the transmitter 85 via the antenna 16 to the antenna 101 of the receiver 102 of the external equipment. When the signal 98 is received by the receiver 102, an alarm means 111 is triggered which informs the patient by audio (and possibly visible) means that: (1) his implanted equipment indicates that he may be having a heart attack or that the patient operated initiator 95 has been used to release medication; (2) he should take some previously agreed upon medication(s) such as aspirin, heparin, nitroglycerin or even be injected with a thrombolytic or anti-thrombogenic agent; (3) an emergency rescue service has been called; and (4) he should either immediately go to a hospital emergency room or he should wait for an ambulance with paramedics to arrive. Within the signal 98 is a patient identification code as well as the patient's real time and stored electrogram. The radio signal 98 that is fed into the receiver 102 would then be an input into the modem 103 that would cause the telephone 104 to send a telephone message 105 to the telephone 106 located at a rescue service 107 typically where an ambulance is located. The rescue service 107 would typically have from the patient's identification code and also all pertinent medical history of the patient as well as an indication that he has suffered a myocardial infarction or that he has initiated medication release to treat a stroke. The real time and stored electrogram 87 would also be received by the rescue service 107. Upon reception of such a radio signal 98, the rescue service 107 would cause an ambulance to be sent to bring the patient to an emergency medical care facility. The external equipment consisting of the antenna 101, the receiver 102, the modem 103, the telephone 104 and the alarm means 111 would be typically located within 200 meters of where the patient would spend most of his time, typically this would be at his residence or possibly at a nursing home. The rescue service would be in reasonably close proximity to where the patient would spend most of his time. If the start of a myocardial infarction is indicated, the patient could be aroused by the alarm means 111, even from sleep, to prepare for an ambulance to come to his home to take him to an emergency care facility. It is also conceivable that a companion or spouse of the myocardial infarction or stroke victim could take the patient to an emergency facility for treatment without waiting for the ambulance to arrive. If this were done, some simple means to inform the rescue service to not send an ambulance could be accomplished by telephone or by other means within the external equipment. Within a nursing home or hospital, a central monitoring station could monitor several patients who have such implanted systems.

Returning now to other implanted equipment shown in FIG. 9, the timing circuits 89 would provide all timing signals required for the operation of the implanted equipment. Also, the alarm means 112 in the implanted portion of the equipment can use an audio or subcutaneous electrical tickle means to inform the patient that an event has occurred such as a myocardial infarction or an episode of ventricular fibrillation or medication has been released to treat a stroke and therefore the patient should see his doctor. The electrical tickle could be provided by an electrode attached to the case 22 that is electrically insulated from the case 22. Audio and electrical tickle alarm means as well as electrogram storage means are described in some detail in U.S. Pat. No. 4,295,474 by R. E. Fischell.

It should also be understood that the implanted and external equipment shown in FIG. 9 could be used with implanted defibrillator circuitry 200 that would have the conventional capability for shocking the heart when ventricular fibrillation is detected and would also have the capability to detect an ST segment deviation indicative of a myocardial infarction. Conventional defibrillators are described in U.S. Pat. No. 4,407,288 by A. A. Langer, et al plus many other U.S. patents. Still another valuable embodiment of the invention is to have an implanted cardiac pacemaker circuitry 300 which has the additional capability for detection of a heart attack, Conventional pacemakers are described in many U.S. patents including U.S. Pat. Nos. 3,867,950 and 3,888,260 by R. E. Fischell. Either of these embodiments would also have the capability of informing the patient by either or both the implantable alarm means 112 or the external alarm means 111 that a myocardial infarction has been detected and or that the patient operated initiator 95 has been used to trigger the release of medication for the treatment of a stroke. When the patient recognizes that he has an indication of a myocardial infarction or a stroke, he could take medication such as aspirin or he could possibly have medication (such as heparin or low molecular weight heparin) injected into his body. Furthermore, the external alarm means 111 could act as an alarm to wake the patient from sleep and can also be used to inform a rescue service 107 using the external equipment shown in FIG. 9. It is of course possible to have both defibrillation and pacemaker capability to which the capability has been added for early detection of a myocardial infarction and treatment for the early symptoms of a stroke The patient operated initiator 95 would typically be retained at all times in close proximity to the patient. For example, in a man's pocket or wallet or in a woman's purse. By using electric watch batteries, the patient operated initiator 95 could indeed be very small and flat. It could also be made as an ornament such as a pendant on a chain around the patient's neck or attached to a bracelet or watchband. To avoid inadvertent actuation of the cardiosaver-strokesaver implant by the patient operated initiator 95, the implanted cardiosaver-strokesaver might only recognize a signal that was on for a least one second, then off for between one and five seconds and then on again for at least one second. Or alternatively, the cardiosaver-strokesaver might only be triggered when the patient operated initiator 95 was pressed three consecutive times within a five to ten second period. Any combination of using one's finger to have a series of on-times and off-times to trigger the cardiosaver-strokesaver is envisioned as an effective means to avoid the inadvertent release of medication.

Figure 10:
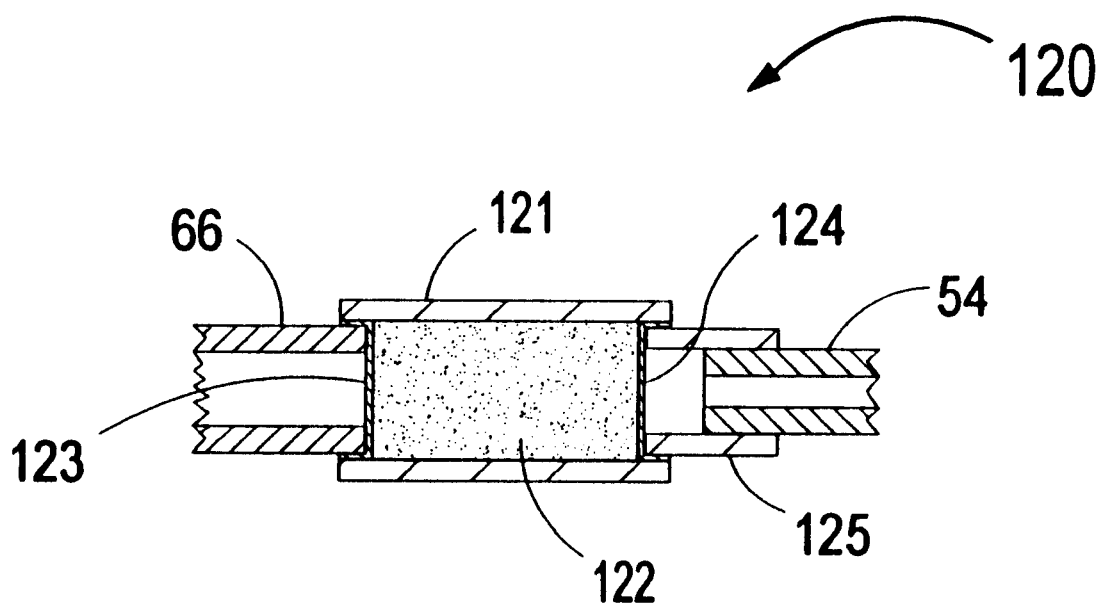
FIG. 10 is a longitudinal cross section of a sealed chamber for storing a thrombolytic and/or anti-thrombogenic agent in powder form prior to that powder being released into the patient's bloodstream.

FIG. 10 is a highly enlarged cross section of a particular embodiment of one portion of the present invention that allows the use of a thrombolytic and or anti-thrombogenic agent in powder form to be used with the medication release device 20. Specifically, FIG. 10 shows a cartridge 120 consisting of a thin-walled metal cylinder 121 that seals a proximal diaphragm 123 against the tube 66 (see FIG. 7) and a distal diaphragm 124 against an extension tube 125 that is joined to the output tube 54. Within the cylinder 121 is (for example) a thrombolytic agent 122 (such as streptokinase) in powder form. The diaphragms 123 and 124 are sufficiently fragile so that they will fracture at a pressure at or above approximately 30 psi. To achieve this level of fragility, the diaphragms 123 and 124 could be made from a metal foil having thickness of less than 0.01 mm. In spite of being so thin, the foils would still provide a hermetic seal to preclude the exposure of the powder 122 to any moisture prior to the release of pressurized liquid from a reservoir (such as the reservoir 35). Upon the detection of a myocardial infarction, a liquid could be released under a very high pressure to fracture both diaphragms 123 and 124 and cause the powder 122 to be released into the patient's bloodstream. As many as three such capsules 120 containing a powdered thrombolytic agent might be placed within the implanted medication release device 20 to be released on three separate occasions when separate myocardial infarctions or early stroke symptoms would be detected. The reservoir fluid to release the powder 122 could be distilled water, or a normal saline solution, or any other solution that would cause no ill effect when released into the bloodstream. It should also be understood that the diaphragms 123 and 124 could have one or more scoring marks on their surface to make them easier to fracture when a fluid pressure is applied.

It is also envisioned that the human subject in whom the cardiosaver-strokesaver is implanted could have the release of medication initiated only under the control of his or her physician. For example, if an alarm was triggered as a result of the detection of a myocardial infarction, then a physician would be called who could review the patient's electrogram over a telephone circuit. The physician could then initiate a command to release medication to treat the myocardial infarction. A command remotely initiated by a physician for medication release if a symptom of a stroke is detected by a patient is also envisioned.

Although the discussion herein has only described a combination medication release system initiated either by a myocardial infarction or a stroke, it is also envisioned that a system designed only to treat stroke is clearly achievable based on the present specification and drawings.

Various other modifications, adaptations, and alternative designs are of course possible in light of the above teachings. Therefore, it should be understood at this time that within the scope of the appended claims the invention can be practiced otherwise than as specifically described herein.

What is claimed is:

1. A medication release system for the treatment of heart attack and/or stroke of a human subject, the medication release system being the combination of an automatic treatment for myocardial infarction and the manual initiation of a treatment for a stroke in response to detection of the early symptoms of such a stroke, the medication release system comprising:

a sensor having an output electrical signal, the sensor being adapted to detect a signal from within the human subject that is indicative of the onset of myocardial infarction;

a patient operated initiator that is adapted to be manually actuated when at least one early symptom of a stroke is detected; and an implanted medication release device that contains electrical circuitry means that is electrically connected to the sensor, the electrical circuitry means being adapted to provide a triggering signal when the output electrical signal from the sensor indicates the occurrence of a myocardial infarction, the medication release device also having at least one medication reservoir for storing a medication and also having a medication releasing means for causing that medication to be released into the bloodstream of the human subject when the triggering signal from the electrical circuitry means indicates that a myocardial infarction is occurring and the electrical circuitry means also being adapted to trigger the release of medication from the medication releasing means when the patient operated initiator is manually actuated.

2. The medication release system of claim 1 wherein the sensor consists of at least two electrodes that are adapted to sense an electrogram from within the human subject.

3. The medication release system of claim 2 wherein at least one electrode is placed inside the right ventricle at or near the apex of the heart.

4. The medication release system of claim 2 wherein at least one electrode is placed in the right atrium.

5. The medication release system of claim 2 wherein at least one electrode is placed in the superior vena cava.

6. The medication release system of claim 2 wherein the medication release device is contained within a metal case and the system includes at least one active electrode and the metal case acts as a second electrode which is an indifferent electrode.

7. The medication release system of claim 1 wherein the sensor includes at least one subcutaneous electrode that is placed outside of the circulatory system of the human subject, the subcutaneous electrode being placed subcutaneously under the skin of the human subject.

8. The medication release system of claim 1 wherein the medication reservoir is formed from a metal bellows.

9. The medication release system of claim 1 wherein the medication in at least one medication reservoir is a thrombolytic agent.

10. The medication release system of claim 9 wherein the thrombolytic agent is streptokinase.

11. The medication release system of claim 9 wherein the thrombolytic agent is urokinase.

12. The medication release system of claim 9 wherein the thrombolytic agent is tissue plasminogen activator.

13. The medication release system of claim 9 wherein the thrombolytic agent is a mixture of two or more medications.

14. The medication release system of claim 1 wherein the medication is an anti-thrombogenic medication.

15. The medication release system of claim 14 wherein the medication is ReoPro.

16. The medication release system of claim 14 wherein the medication is heparin.

17. The medication release system of claim 1 wherein the medication within the medication release device is in the form of a powder.

18. The medication release system of claim 17 wherein the powder is a thrombolytic agent.

19. The medication release system of claim 18 wherein the thrombolytic agent is streptokinase powder.

20. The medication release system of claim 1 wherein there is exactly one medication reservoir.

21. The medication release system of claim 1 wherein there are exactly two medication reservoirs.

22. The medication release system of claim 1 wherein there are exactly three medication reservoirs.

23. The medication release system of claim 1 wherein the medication releasing means is a valve that is opened after the sensor senses the occurrence of a myocardial infarction or when the patient operated initiator is manually activated.

24. The medication release system of claim 1 wherein the medication releasing means is a valve operated by means of changing the polarity of a chargeable magnet.

25. The medication release system of claim 1 wherein the medication releasing means is a conventional drug pump.

26. The medication release system of claim 1 wherein the electrical circuitry means includes the capability for recording the electrogram and playing back the electrogram at a later time.

27. The medication release system of claim 1 wherein the electrical circuitry means includes a command receiver for receiving programming commands by radio transmission from a physician's programmer that is located externally from the human subject, the programming commands being capable of changing the operating modes of the medication release system.

28. The medication release system of claim 1 wherein the electrical circuitry means includes a radio transmitter for transmitting information from the implanted medication release system to a physician's programmer.

29. The medication release system of claim 1 wherein the electrical circuitry means includes a radio transmitter for transmitting information to a receiver that is located within 200 meters of the human subject, the receiver being adapted to cause an alarm means to inform the human subject that his implanted medication release system has sensed the occurrence of a myocardial infarction.

30. The medication release system of claim 1 wherein the electrical circuitry means includes a radio transmitter for transmitting information to a receiver that is located within 200 meters of the human subject, the receiver being adapted to send a message to a medical rescue facility that the medication release system within the human subject has sensed the occurrence of a myocardial infarction or has triggered the release of medication by manual actuation of the patient operated initiator.

31. The medication release system of claim 30 wherein the message received by the medical rescue facility includes the electrogram of the human subject.

32. The medication release system of claim 30 wherein the message received by the medical rescue service includes at least one of the following group of data: the medical history of the human subject, the address of the human subject and the directions to the location of the human subject.

33. The medication release system of claim 1 further comprising defibrillation means operated from automatic defibrillation circuitry implanted within the human subject.

34. The medication release system of claim 1 further comprising implantable heart pacemaker circuitry for pacing the heart of the human subject by means of electrical pulses.

35. The medication release system of claim 1 wherein the electrical circuitry means includes the capability for alarming the human subject that a myocardial infarction is occurring by causing an audio sound to be produced that can be heard by the human subject.

36. The medication release system of claim 1 wherein the electrical circuitry means includes the capability of alarming the human subject that a myocardial infarction is occurring by means of a subcutaneous electrical tickle that can be detected by the human subject.

37. The medication release system of claim 1 wherein the patient operated initiator is located external to the human subject, the patient operated initiator being adapted to send a radio signal to a command receiver within the medication release device, the radio signal being adapted to cause the release of medication from the implanted medication release device.

38. The medication release system of claim 37 wherein the patient operated initiator is adapted to be activated by the human subject or by a patient caregiver of the human subject when at least one symptom of a stroke is detected.

39. The medication release system of claim 1 wherein the patient operated initiator is activated by a predetermined sequence of actuation on-times and off-times, which predetermined sequence is recognized by the electronic circuitry means of the implanted portion of the medication release system.

* * * * *